(12) United States Patent
Zottola

(10) Patent No.: US 10,506,940 B2
(45) Date of Patent: Dec. 17, 2019

(54) STIMULATION PROGAMMING AID USING A SENSORY PROJECTION

(71) Applicant: Boston Scientific Neuromodulation Corporation, Valencia, CA (US)

(72) Inventor: Dennis Zottola, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/729,851

(22) Filed: Oct. 11, 2017

(65) Prior Publication Data

US 2018/0110435 A1 Apr. 26, 2018

Related U.S. Application Data

(60) Provisional application No. 62/412,566, filed on Oct. 25, 2016.

(51) Int. Cl.
*A61B 5/0476* (2006.01)
*A61B 5/00* (2006.01)
*A61B 5/11* (2006.01)
*A61N 1/36* (2006.01)

(52) U.S. Cl.
CPC .......... *A61B 5/0476* (2013.01); *A61B 5/0031* (2013.01); *A61B 5/11* (2013.01); *A61B 5/486* (2013.01); *A61B 5/686* (2013.01); *A61B 5/0022* (2013.01); *A61N 1/36067* (2013.01)

(58) Field of Classification Search
USPC ...................................... 607/57, 62
See application file for complete search history.

(56) References Cited

U.S. PATENT DOCUMENTS

| 8,112,154 B2 | 2/2012 | Rezai et al. | |
| 8,700,168 B1* | 4/2014 | Johnston | A61N 1/36032 607/57 |
| 2006/0100672 A1* | 5/2006 | Litvak | A61N 1/36036 607/57 |
| 2008/0103559 A1* | 5/2008 | Thacker | A61N 1/36146 607/62 |
| 2011/0029044 A1* | 2/2011 | Hyde | A61B 5/6804 607/62 |
| 2013/0184780 A1 | 7/2013 | Pless et al. | |

* cited by examiner

*Primary Examiner* — Nicole F Lavert
(74) *Attorney, Agent, or Firm* — Schwegman Lundberg & Woessner, P.A.

(57) ABSTRACT

This document discusses, among other things, systems and methods to map an electrical waveform to a user-perceivable input. Some system examples include at least one electrode configured to sense neural activity in a patient, a mapping controller configured to receive an electrical waveform from the at least one electrode and map the sensed neural activity to a user-perceivable output based on the sensed neural activity, and a user interface operably connected to the mapping controller and configured to provide the user-perceivable output to a user.

19 Claims, 5 Drawing Sheets

STIMULATION PROGAMMING AID USING A SENSORY PROJECTION

CLAIM OF PRIORITY

This claims the benefit of priority under 35 U.S.C. § 119(e) of U.S. Provisional Patent Application Ser. No. 62/412,566, filed on Oct. 25, 2016, which is herein incorporated by reference in its entirety.

TECHNICAL FIELD

This document relates generally to medical devices, and more particularly, to systems, devices and methods for delivering neural stimulation or sensing neural activity.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy. Neurostimulation may also be provided by a non-implantable neurostimulator.

Neurostimulation energy may be delivered using electrical energy that may be controlled using stimulation parameters that specify spatial (where to stimulate), temporal (when to stimulate), and informational (stimulation patterns directing the nervous system to respond as desired) aspects of a pattern of neurostimulation waveforms.

SUMMARY

An example (e.g., "Example 1") of subject matter (e.g., an apparatus) may include at least one electrode configured to sense neural activity in a patient, a mapping controller configured to receive an electrical waveform from the at least one electrode and map the sensed neural activity to an electrical representation of a user-perceivable output based on the sensed neural activity, and a user interface operably connected to the mapping controller and configured to provide the user-perceivable output to a user.

In Example 2, the subject matter of Example 1 may optionally be configured such that the user-perceivable output includes at least one of an audio waveform, a haptic waveform, or a color waveform.

In Example 3, the subject matter of any one or any combination of Examples 1-2 may optionally be configured such that the sensed neural activity includes amplitudes and frequencies, and the mapping controller is further configured to use the amplitudes and frequencies to generate the user-perceivable output.

In Example 4, the subject matter of any one or any combination of Examples 1-3 may optionally be configured such that the mapping controller includes a first mapping function for efferent neural waveforms and a second mapping function for afferent neural waveforms.

In Example 5, the subject matter of any one or any combination of Examples 1-4 may optionally be configured such that the user interface includes haptic feedback circuitry configured to provide a haptic waveform corresponding to efferent neural waveforms to a first body location of the user and provide a haptic waveform corresponding to afferent neural waveforms to a second body location of the user.

In Example 6, the subject matter of any one or any combination of Examples 1-5 may optionally be configured such that mapping the sensed neural activity includes scaling the sensed neural activity.

An example (e.g., "Example 7") of subject matter (e.g., an apparatus) may include a user interface configured to receive a user-perceivable input from a user and deliver an electrical representation of the user-perceivable input to a mapping controller, a mapping controller configured to map an electrical representation of a user-perceivable input to an electrical waveform and to deliver the electrical waveform to at least one electrode, and at least one electrode configured to provide neurostimulation.

In Example 8, the subject matter of Example 7 may optionally be configured such that the user-perceivable input includes at least one of an audio waveform, a haptic waveform, or a color waveform.

In Example 9, the subject matter of any one or any combination of Examples 7-8 may optionally be configured such that the user-perceivable input contains amplitude and frequency parameters of the delivered electrical waveform.

In Example 10, the subject matter of any one or any combination of Examples 7-9 may optionally be configured such that the mapping controller includes a first mapping function for efferent neural waveforms and a second mapping function for afferent neural waveforms.

In Example 11, the subject matter of any one or any combination of Examples 7-10 may optionally be configured such that the user-perceivable input includes a haptic waveform having portions corresponding to efferent neural waveforms and to afferent neural waveforms.

In Example 12, the subject matter of any one or any combination of Examples 7-11 may optionally be configured such that the user interface is further configured to deliver the user-perceivable input as a user-perceivable output to the user before the mapping controller delivers the electrical waveform to the at least one electrode.

In Example 13, the subject matter of Example 12 may optionally be configured such that the user interface is further configured to receive, from the user, a confirmation in response to the user-perceivable output and the mapping controller is further configured to deliver the electrical waveform to the at least one electrode in response to the received confirmation.

An example (e.g., "Example 14") of subject matter (e.g., an apparatus) may include at least one electrode configured to sense neural activity in a patient, to receive an electrical waveform, and to provide neurostimulation to the patient, a mapping controller configured to receive an electrical waveform from the at least one electrode and map the sensed neural activity to an electrical representation of a user-perceivable output based on the sensed neural activity and map an electrical representation of a user-perceivable input to an electrical waveform and deliver the electrical waveform to the at least one electrode, and a user interface operably connected to the mapping controller and configured to provide the user-perceivable output to a user and receive a user-perceivable input from a user and deliver an electrical representation of the user-perceivable input to the mapping controller.

In Example 15, the subject matter of Example 14 may optionally be configured such that the user-perceivable input includes at least one of an audio waveform, a haptic waveform, or a color waveform.

An example (e.g., "Example 16") of subject matter (e.g., a method) may include delivering an electrical representation of a user-perceivable input, mapping the received electrical representation of the user-perceivable input to an electrical waveform, and delivering the electrical waveform to at least one electrode, the at least one electrode configured to deliver neurostimulation to the patient.

In Example 17, the subject matter of Example 16 may optionally be configured such that the user-perceivable input includes at least one of an audio waveform, a haptic waveform, or a color waveform.

In Example 18, the subject matter of Example 17 may optionally be configured such that the user-perceivable input contains amplitude and frequency parameters of the delivered electrical waveform.

In Example 19, the subject matter of Example 18 may optionally be configured such that the mapping includes a first mapping function for efferent neural waveforms and a second mapping function for afferent neural waveforms.

In Example 20, the subject matter of Example 18 may optionally be configured such that the user-perceivable input includes a haptic waveform having portions corresponding to efferent neural waveforms and to afferent neural waveforms.

An example (e.g., "Example 21") of subject matter (e.g., a method) may include receiving an electrical waveform from at least one electrode, the at least one electrode configured to sense neural activity in a patient, storing the received electrical waveform in a memory, mapping the received electrical waveform to an electrical representation of a user-perceivable output, and producing the mapped user-perceivable output to a first user, the produced user-perceivable output being indicative of a healthy or diseased neural activity.

In Example 22, the subject matter of Example 21 may optionally be configured such that the user-perceivable output includes at least one of an audio waveform, a haptic waveform, or a color waveform.

In Example 23, the subject matter of Example 21 may optionally be include storing the electrical representation of the user-perceivable output in a memory, transmitting the electrical representation of the user-perceivable output and a mapping function to a user interface, and producing the mapped user-perceivable output to a second user based on the transmitted electrical representation of the user-perceivable output and the mapping function.

In Example 24, the subject matter of Example 23 may optionally be configured such that the mapping includes a first mapping function for efferent neural waveforms and a second mapping function for afferent neural waveforms.

In Example 25, the subject matter of Example 23 may optionally be configured such that the user-perceivable output includes a haptic waveform and the haptic waveform corresponding to efferent neural waveforms is provided to a first body location of the user and the haptic waveform corresponding to afferent neural waveforms is provided to a second body location of the user.

An example (e.g., "Example 26") of subject matter (e.g., an apparatus) may include at least one electrode configured to sense neural activity in a patient, a mapping controller configured to receive an electrical waveform from the at least one electrode and map the sensed neural activity to an electrical representation of a user-perceivable output based on the sensed neural activity, and a user interface operably connected to the mapping controller and configured to provide the user-perceivable output to a user.

In Example 27, the subject matter of Example 26 may be optionally be configured such that the user-perceivable output includes at least one of an audio waveform, a haptic waveform, or a color waveform.

In Example 28, the subject matter of Example 27 may be optionally be configured such that the user-perceivable output is generated based on amplitudes and frequencies of the neural activity.

In Example 29, the subject matter of Example 26 may be optionally be configured such that the mapping controller includes a first mapping function for efferent neural waveforms and a second mapping function for afferent neural waveforms.

In Example 30, the subject matter of Example 29 may be optionally be configured such that the user interface includes haptic feedback circuitry configured to provide a haptic waveform corresponding to efferent neural waveforms to a first body location of the user and provide a haptic waveform corresponding to afferent neural waveforms to a second body location of the user.

An example (e.g., "Example 31") of subject matter (e.g., an apparatus) may include at least one electrode configured to provide neurostimulation, a mapping controller configured to map an electrical representation of a user-perceivable input to an electrical waveform and deliver the electrical waveform to the at least one electrode, and a user interface configured to receive a user-perceivable input from a user and deliver an electrical representation of the user-perceivable input to the mapping controller.

In Example 32, the subject matter of Example 31 may optionally be configured such that the user-perceivable input includes at least one of an audio waveform, a haptic waveform, or a color waveform.

In Example 33, the subject matter of Example 31 may optionally be configured such that the mapping controller includes a first mapping function for efferent neural waveforms and a second mapping function for afferent neural waveforms.

In Example 34, the subject matter of Example 31 may be optionally be configured such that the user-perceivable input includes a haptic waveform having portions corresponding to efferent neural waveforms and to afferent neural waveforms.

An example (e.g., "Example 35") of subject matter (e.g., an apparatus) may include at least one electrode configured to sense neural activity in a patient and to receive an electrical waveform and provide neurostimulation to a patient, a mapping controller configured to receive an electrical waveform from the at least one electrode and map the sensed neural activity to an electrical representation of a user-perceivable output based on the sensed signal and map an electrical representation of a user-perceivable input to an electrical waveform and provide neurostimulation by delivering the electrical waveform to the at least one electrode, and a user interface operably connected to the mapping controller and configured to provide the user-perceivable output to a user and receive a user-perceivable input from a user and deliver an electrical representation of the user-perceivable input to the mapping controller.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., such as a non-transitory medium or a medium having a mass) including instructions that, when performed by a machine, cause the machine to perform any portion of any one or more of the functions or methods of Examples 1-35.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The above detailed description is intended to be illustrative, and not restrictive. The scope of the disclosure should, therefore, be determined with references to the appended claims, along with the full scope of equivalents to which such claims are entitled.

Certain neurostimulation systems may sense neural activity in a patient as an electrical waveform and may provide a graphical representation of the electrical waveform to a user. The user may review the electrical waveform to determine if there are irregularities or undesirable features. However, such an electrical waveform may be complex (e.g., the electrical waveform may include pulses, bursts of pulses, trains of bursts, and sequences of pulses, bursts, and trains) and it may be difficult for the user to recognize patterns within the graphical representation. The electrical waveform may include a distribution of frequencies and amplitudes. The inventor has recognized, among other things, that it is possible to provide alternative representations of the measured neural activity, such as audio, haptic, or color representations that may provide an improved method of analyzing the measured neural activity and programming a neural stimulation system.

Figure 1A:
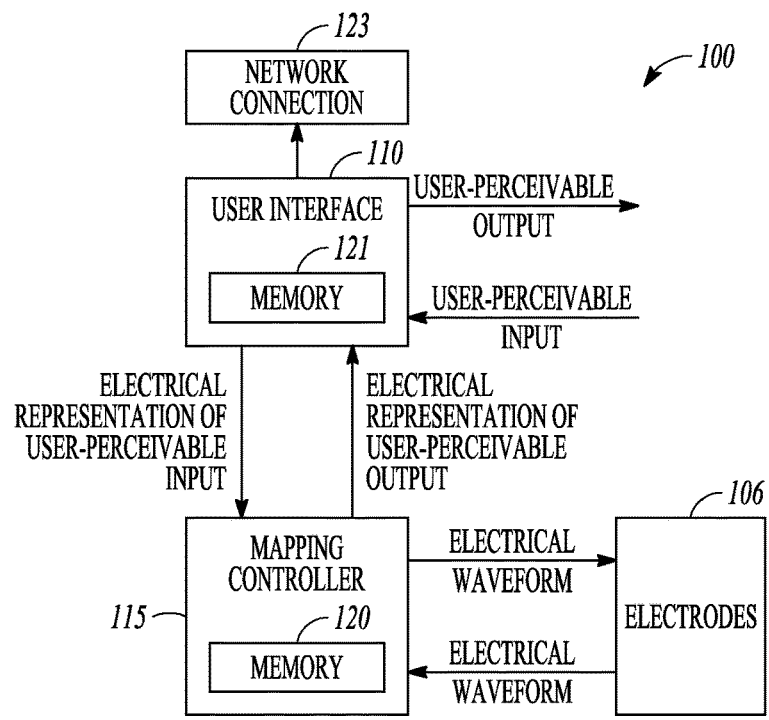
FIG. 1A illustrates an example of a neurostimulation system.
Figure 1B:
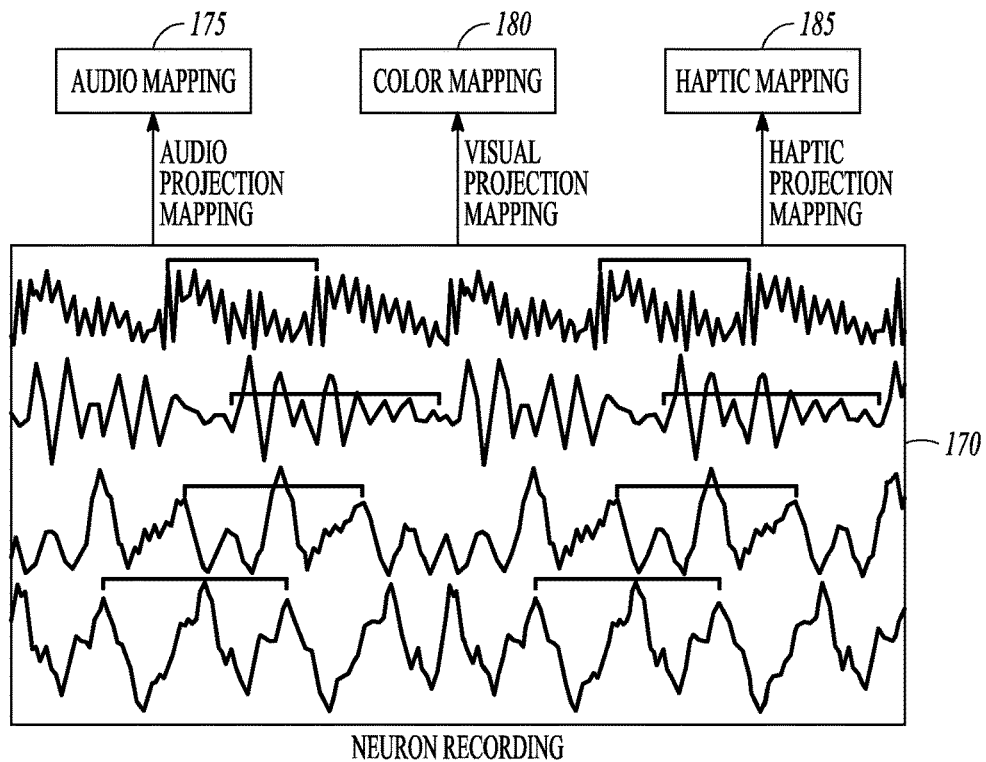
FIG. 1B illustrates multiple examples of a mapping of an electrical waveform.

FIG. 1A illustrates by way of example, and not limitation, an embodiment of a neurostimulation system 100. The neurostimulation system 100 may include a user interface 110, a mapping controller 115, and electrodes 106. The user interface 121 may include a memory 110. The user interface may include a network connection 123. The mapping controller 115 may include a memory 120 and processing circuitry. The neurostimulation system 100 may receive an input from a user and provide a neurostimulation to the patient based on the received input. The user interface 110 may allow the user to provide a user-perceivable input such as an audio signal, a color signal, or haptic signal. The user interface 110 may provide an electrical representation of the received user-perceivable input to the mapping controller 115. The mapping controller 115 may store the received electrical representation in a memory 120. In an example, the mapping controller 115 may store the received electrical representation in a file, in the memory 120. The stored file may be shared with other users. The other users may play the stored file with a user interface, such as the user interface 110. The mapping controller 115 may then transform the received electrical representation into an electrical waveform. The mapping controller 115 may then deliver the electrical waveform to the electrodes 106 to provide a neurostimulation to the patient. The user interface 110 may be configured to allow the user to review the user-perceivable input before the mapping controller provides the electrical waveform to the electrodes 106. The neurostimulation system 100 may provide an output to a user based on a neurostimulation signal received from the patient. The electrodes 106 in cooperation with neural sensing circuitry may sense a neural activity in the patient. The sensed neural activity may be provided as an electrical waveform to the mapping controller 115 and stored in the memory 120. The mapping controller 115 may transform the received electrical waveform into an electrical representation of a user-perceivable output, such as an audio representation of the electrical waveform. In an example, the mapping controller 115 may store the electrical representation in a file, in the memory 120. The stored file may be shared with other users, such as to provide therapeutic guidance for various diseased neural states. The other users may play the stored file with a user interface, such as the user interface 110. The mapping controller 115 may transform the received electrical waveform into an electrical representation of a user-perceivable output, such as a color representation of the electrical waveform. The mapping controller 115 may transform the received electrical waveform into an electrical representation of a user-perceivable output, such as a haptic representation of the electrical waveform. The mapping controller 115 may use a mapping function to transform the received electrical waveform into an electrical representation of a user-perceivable output. The mapping function may be provided by the user, and may determine the correspondence between the received electrical waveform and the user perceivable output. The electrical representation of the user-perceivable output may then be provided to the user interface 110 and the user interface 110 may then provide a user-perceivable output to the user. The electrical representation of the user-perceivable output may be stored in the memory 110. The stored electrical representation of the user-perceivable output may be shared with other users. For example, the user interface 110 may transmit the stored electrical representation of the user-perceivable output to other users over the network connection 123 (e.g., a local area network connection, a wide area network connection, or a connection to the Internet). The other users may observe the shared user-perceivable output using a user interface, such as the user interface 110. A mapping function that describes the correspondence between the electrical representation of the user-perceivable output and the received electrical waveform may also be stored in the memory 110 and may be transmitted to the other users. The mapping function may be transmitted to the other users together with the stored electrical representation of the user-perceivable output. As shown in FIG. 1B, the received electrical waveform, such as electrical waveform 170 may be relatively complex and may include pulses, bursts of pulses, trains of bursts, and sequences of pulses, bursts, trains, and a distribution of amplitudes and frequencies, and may not be easily interpreted by a user. In an example, a saved file corresponding to a mapped neurostimulation signal received from a patient may be overlaid with a mapped neurostimulation signal being received in real-time from a patient. In such an example, the saved file may correspond to a mapped neurostimulation signal received from a healthy patient (e.g., the mapped neurostimulation signal can represent healthy neural activity) and the mapped signal being received in real-time may be received from a diseased patient. In an example, a user interface, such as user interface 110 may provide a difference between the saved file and the mapped neurostimulation signal received in real-time, and the provided difference may be indicative of unhealthy neural activities. In an example, neural stimulation may be provided to the patient, such as by using the stimulation device 104 and electrodes 106 to eliminate the identified unhealthy neural activities, such as those corresponding to the difference between the saved file and the mapped neurostimulation signal received in real-time. In an example, neural stimulation may be provided to the patient, such as by using the stimulation device 104 and electrodes 106 to cause the mapped neurostimulation signal received in real-time to match the saved file.

The mapping controller 115 may provide an audio mapping 175 of the complex electrical waveform, such as to provide a user-perceivable output that may be easier to interpret than a graphical representation of an electrical waveform, such as the electrical waveform 170. The mapping controller 115 may provide a color mapping 180 of the complex electrical waveform, such as to provide a user-perceivable output that may be easier to interpret than a graphical representation of an electrical waveform, such as the electrical waveform 170. The mapping controller 115 may provide a haptic mapping 185 of the complex electrical waveform, such as to provide a user-perceivable output that may be easier to interpret than a graphical representation of an electrical waveform, such as the electrical waveform 170.

In an example where the user perceivable input includes an audio signal, the user interface 110 may include a touch screen and the user may compose an audio signal by dragging and dropping musical notes onto one or more musical staffs displayed by the touch screen. The user may indicate a relative strength of each note (e.g., the user may assign a numerical value to each note). The one or more musical staffs may correspond to different musical instruments. After the user completes the composition, the user interface 110 may provide the composed audio signal to the user, such as by converting the composed audio signal into a pressure wave, for example, with a pressure transducer. After listening to the composed audio signal, the user may provide a confirmation before an electrical representation of the composed audio signal is delivered to the mapping controller 115. The mapping controller may receive the electrical representation of the composed audio signal and map the composed audio signal to an electrical waveform. The mapping controller may map each musical note to a frequency, or a group of frequencies (e.g., a group of frequencies corresponding to a particular musical instrument, such as a violin or a piano) of an electrical waveform. The mapping controller may map each musical note to an amplitude based on the numerical values provided by the user. The mapping controller may scale the composed audio signal such that the frequencies represented by the musical notes are increased or decreased such as to provide an efficient neurostimulation (e.g., the mapping controller may increase the frequencies represented by each of the musical notes by 5). The mapping controller may then deliver the mapped electrical waveform to the patient via the electrodes 106 to provide neurostimulation to the patient. The mapped electrical waveform may include a frequency distribution, amplitude distribution, a number of pulses, burst of pulses, trains of bursts, sequences of pulses, bursts, and trains.

In an example where the user perceivable output includes an audio signal, the mapping controller may receive an electrical waveform representative of neural activity of the patient from the electrodes 106 and associated neural sensing circuitry. The mapping controller may then map the electrical waveform to an electrical representation of an audio signal. The mapping controller may map the received electrical waveform to a collection of musical notes, where each note may represent a frequency or a group of frequencies of the electrical waveform (e.g., a group of frequencies corresponding to a particular musical instrument, such as a violin or a piano). The mapping controller may assign a numerical value to each of the musical notes based on the amplitude of the electrical waveform. The mapping controller may assign a first family of instruments to afferent neural signals and a second family of instruments to efferent neural signals (e.g., the mapping controller may assign wind instruments to afferent neural signals and string instruments to efferent neural signals). The mapping controller may provide the mapped electrical representation of the audio signal to the user interface 110. The user interface 110 may provide the mapped representation of the audio signal to the user, such as by converting the audio signal into a pressure wave, for example, with a pressure transducer. The user may listen to the provided audio signal, such as to determine healthy or diseased neural activity of the patient.

In an example where the user perceivable input includes a haptic signal, the user interface 110 may include a touch screen and the user may compose a haptic signal by dragging and dropping elements within the touchscreen. The user may indicate a relative strength of each element (e.g., the user may assign a numerical value to each element). Each element may correspond to a haptic signal having a frequency distribution, amplitude distribution, a number of pulses, burst of pulses, trains of bursts, sequences of pulses, bursts, and trains. The user may request, such as by selecting an element, that a haptic signal corresponding to the element be provided to the user. The user interface may provide the requested haptic signal to the user, such as by providing the haptic signal to a vibratory element. After the user completes the composition, the user interface 110 may provide the composed haptic signal to the user, such as by providing the composed haptic signal to a vibratory element. After feeling the composed haptic signal, the user may provide a confirmation before an electrical representation of the composed haptic signal is delivered to the mapping controller 115. The mapping controller may receive the electrical representation of the composed haptic signal and map the composed haptic signal to an electrical waveform. The mapping controller may map each element to a frequency, or a group of frequencies of an electrical waveform. The mapping controller may set an amplitude based on the numerical values provided by the user. The mapping controller may scale the composed haptic signal such that the frequencies represented by the haptic signal are increased or decreased such as to provide an efficient neurostimulation (e.g., the mapping controller may increase the frequencies represented by each of the elements by 5). The mapping controller may then deliver the mapped electrical waveform to the patient via the electrodes 106 to provide neurostimulation to the patient. The mapped electrical waveform may include a frequency distribution, amplitude distribution, a number of pulses, burst of pulses, trains of bursts, sequences of pulses, bursts, and trains.

In an example where the user perceivable output includes a haptic signal, the mapping controller may receive an electrical waveform representative of neural activity of the patient from the electrodes 106 and associated neural sensing circuitry. The mapping controller may then map the electrical waveform to an electrical representation of a haptic signal. The mapping controller may map the received electrical waveform to a collection of elements, where each element may represent a frequency or a group of frequencies of the electrical waveform. The mapping controller may assign a numerical value to each of the elements based on the amplitude of the electrical waveform. The mapping controller may assign each element to a body part. For example, a first element corresponding to an afferent neural waveform may be assigned to a first body part and a second element corresponding to an efferent neural waveform may be assigned to a second body part. The mapping controller may provide the mapped electrical representation of the haptic signal to the user interface 110. The user interface 110 may provide the mapped representation of the haptic signal to the user, such as by providing the haptic signal to at least one vibratory element, for example, with a piezoelectric element. The vibratory element may provide sheer forces to stimulate the user's Pacinian corpuscles. The user interface 110 may provide the haptic waveform corresponding to a first element to a first vibratory element at a first body location (e.g., right arm) and a second element to a second vibratory element at a second body location (e.g., left arm).

In an example where the user perceivable input includes a color signal, the user interface 110 may include a touch screen and the user may compose a color signal by selecting colors from a color palette and assigning colors to an electronic canvas on the touchscreen. The electronic canvas may include an array of pixels. The color of each pixel may be designated by the user. Each color may include a hue, a saturation, and a brightness. Each pixel may correspond to a frequency distribution, amplitude distribution, a number of pulses, burst of pulses, trains of bursts, sequences of pulses, bursts, and trains of an electrical waveform. An electrical representation of the composed color signal may be delivered to the mapping controller 115. The mapping controller may receive the electrical representation of the composed color signal and map the composed color signal to an electrical waveform. The mapping controller may map each pixel to a frequency and amplitude, or a group of frequencies and amplitudes of an electrical waveform based on the hue, saturation, brightness, and position of each pixel. The mapping controller may scale the composed color signal such that the frequencies represented by the color signal are increased or decreased such as to provide an efficient neurostimulation (e.g., the mapping controller may increase the frequencies represented by each of the pixels by 5). The mapping controller may then deliver the mapped electrical waveform to the patient via the electrodes 106 to provide neurostimulation to the patient.

In an example where the user perceivable output includes a color signal, the mapping controller may receive an electrical waveform representative of neural activity of the patient from the electrodes 106 and associated neural sensing circuitry. The mapping controller may then map the electrical waveform to an electrical representation of a color signal. The mapping controller may map the received electrical waveform to an array of pixels. Each pixel may include a color, and may represent a frequency distribution, amplitude distribution, a number of pulses, burst of pulses, trains of bursts, sequences of pulses, bursts, and trains of an electrical waveform. Each color may include a hue, a saturation, and a brightness. The mapping controller may map a frequency and amplitude, or a group of frequencies and amplitudes of an electrical waveform such as to determine a hue, saturation, and brightness for each pixel in the array of pixels. The mapping controller may map complimentary colors to afferent neural signals and efferent neural signals (e.g., the mapping controller may map efferent neural signals to yellow color and afferent neural signals to a violet color in a traditional RYB color model). The mapping controller may provide the mapped electrical representation of the color signal to the user interface 110. The user interface 110 may provide the mapped representation of the color signal to the user, such as with a display screen.

Figure 1C:
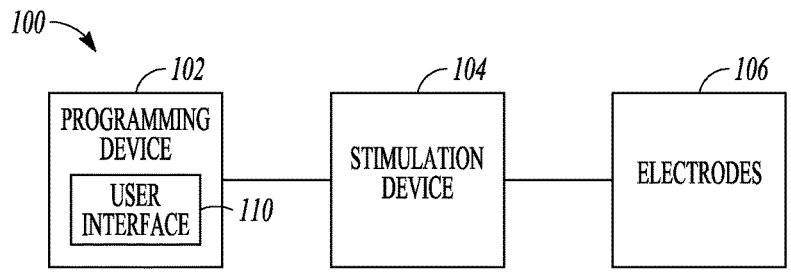
FIG. 1C illustrates an example of a neurostimulation system.

FIG. 1C illustrates, by way of example and not limitation, an embodiment of a neurostimulation system 100. The neurostimulation system 100 may include electrodes 106, a stimulation device 104, and a programming device 102. The mapping controller 115 may be included in the programming device 102 or the stimulation device 104. The electrodes 106 may be configured to be placed on or near one or more neural targets in a patient. The stimulation device 104 may be configured to be electrically connected to the electrodes 106 and deliver neurostimulation energy, such as in the form of electrical waveforms, to the one or more neural targets through the electrodes 106. The delivery of the neurostimulation may be controlled using a plurality of stimulation parameters, such as stimulation parameters specifying a waveform shape. For example, stimulation parameters may include, but are not limited to, a pattern of the electrical waveforms and a selection of electrodes through which each of the electrical waveforms may be delivered. At least some parameters of the plurality of stimulation parameters may be determined by a user-perceivable input, such as a user-perceivable input provided by a user, such as a physician or other caregiver who treats the patient using system 100. The programming device 102 may be configured to be communicatively coupled to stimulation device 104 via a wired or wireless link.

The programming device 102 may include a user interface that allows the user to set and/or adjust values of user-programmable parameters by creating and/or editing user-perceivable inputs (e.g., audio, color, or haptic signals). The user-perceivable inputs may represent an electrical waveform, such as an electrical waveform that may be delivered to the electrodes 106, such as to provide a therapy to a patient. Such electrical waveforms may include different waveform shapes. The waveform shapes may include regular shapes (e.g. square, sinusoidal, triangular, saw tooth, and the like) or irregular shapes. The waveform shapes may include regular or irregular patterns. The waveform shapes may be similar to analog signals or may be similar to digitized signals. By way of example and not limitation, the waveforms may include a pattern of temporal waveform segments, which may include a pattern of neurostimulation waveforms, to be delivered to the patient.

Figure 2:
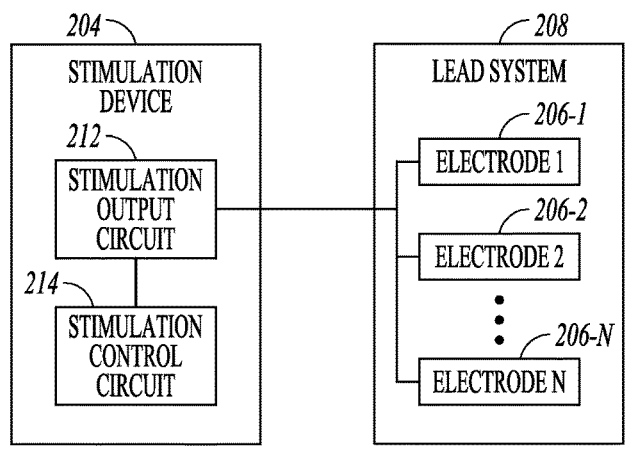
FIG. 2 illustrates and example of a stimulation device and a lead system.

FIG. 2 illustrates, by way of example and not limitation, an embodiment of a stimulation device 204 and a lead system 208, such as may be implemented in neurostimulation system 100. The stimulation device 204 may include a stimulation output circuit 212 and a stimulation control circuit 214. The stimulation output circuit 212 may produce and deliver neurostimulation waveforms. The stimulation control circuit 214 may control the delivery of the neurostimulation waveforms using the plurality of stimulation parameters, which specifies a pattern of the neurostimulation waveform. The stimulation control circuit 214 may control the delivery of neurostimulation waveforms using the user-perceivable input that has been mapped to an electrical waveform by the mapping controller 115. The lead system 208 may include one or more leads each configured to be electrically connected to the stimulation device 204 and a plurality of electrodes 206 distributed in the one or more leads. The plurality of electrodes 206 may include electrode 206-1, electrode 206-2, . . . electrode 206-N, each a single electrically conductive contact providing for an electrical interface between the stimulation output circuit 212 and tissue of the patient, where N≥2. The neurostimulation waveform may be delivered from the stimulation output circuit 212 through a set of electrodes selected from the electrodes 206.

The number of leads and the number of electrodes on each lead may depend on, for example, the distribution of target(s) of the neurostimulation and the need for controlling the distribution of electric field at each target. By way of example and not limitation, the lead system 208 may include two leads each having eight electrodes. Other lead systems, such as but not limited to, four lead systems or paddle leads may be used.

Figure 3:
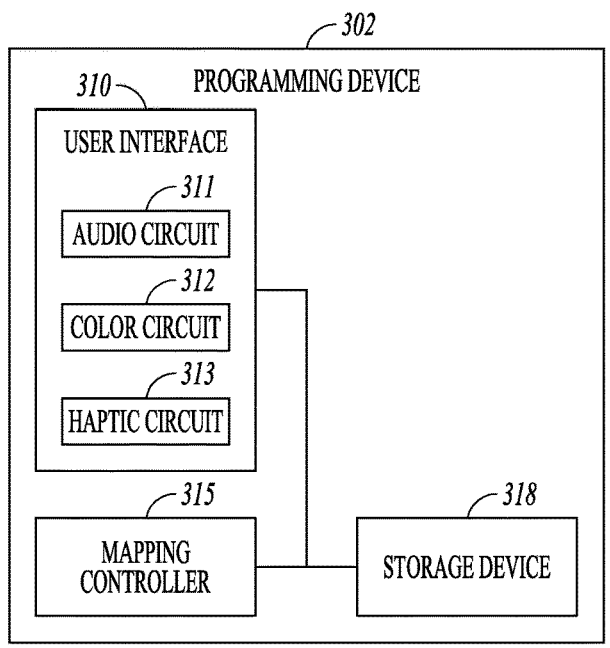
FIG. 3 illustrates an example of a programming device.

FIG. 3 illustrates, by way of example and not limitation, an embodiment of a programming device 302, such as may be implemented in neurostimulation system 100. The programming device 302 may include a storage device 318, a control circuit 311, a mapping controller 315, and a user interface 310. The user interface 310 may include an audio circuit 311, a color circuit 312, and a haptic circuit 313. During operation, a user may provide a user-perceivable input such as an audio representation, a color representation, or a haptic representation of an electrical waveform to the user interface 310. The user interface 310 may include a display screen that allows the user to compose an audio waveform, a haptic waveform, or a color waveform. The user interface may provide the user-perceivable input to the user, such as for the purposes of verification (e.g., if the user-perceivable input includes an audio signal, the user interface may play the audio signal to the user and the user may verify the audio signal). The user interface 310 may provide an electrical representation of the received user-perceivable input to the mapping controller 315. The mapping controller 315 may convert the user-perceivable input into an electrical waveform. The electrical waveform may then be delivered to the electrodes 106, such as to provide a neurostimulation therapy to the patient. Additionally, the user interface 310 may provide an output to a user based on a neurostimulation signal received from the patient. The electrodes 106, in cooperation with neural sensing circuitry, may sense a neural activity of the patient and provide the sensed activity as an electrical waveform to the storage device 318. The storage device may then provide the sensed electrical waveform to the mapping controller 315. The mapping controller 315 may convert the sensed electrical waveform into an electrical representation of a user-perceivable output. The electrical representation of the user-perceivable output may be provided to the user interface and the user interface may provide a user-perceivable output to the user. The user perceivable output may be an audio signal, a haptic signal, or a color signal. The audio circuit 311 may include a transducer, such as to convert an audio signal into a pressure wave, such as to provide an audio output to the user. The haptic circuit 313 may include at least one vibratory element (e.g., a piezoelectric element) for converting a haptic signal into a mechanical vibration, such as to provide a haptic signal to the user.

In an example, user interface 310 may include, but is not limited to, a touchscreen. For example, user interface 310 may include any type of presentation device, such as interactive or non-interactive screens, and any type of user input devices that allow the user to edit the user-perceivable input, such as touchscreen, keyboard, keypad, touchpad, trackball, joystick, and mouse. The circuits of neurostimulation system 100, including its various embodiments discussed in this document, may be implemented using a combination of hardware and software. For example, the circuit of user interface 110 or 310, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit may include, but is not limited to, a microprocessor or a portion thereof, a microcontroller or portions thereof, and a programmable logic circuit or a portion thereof.

Figure 4:
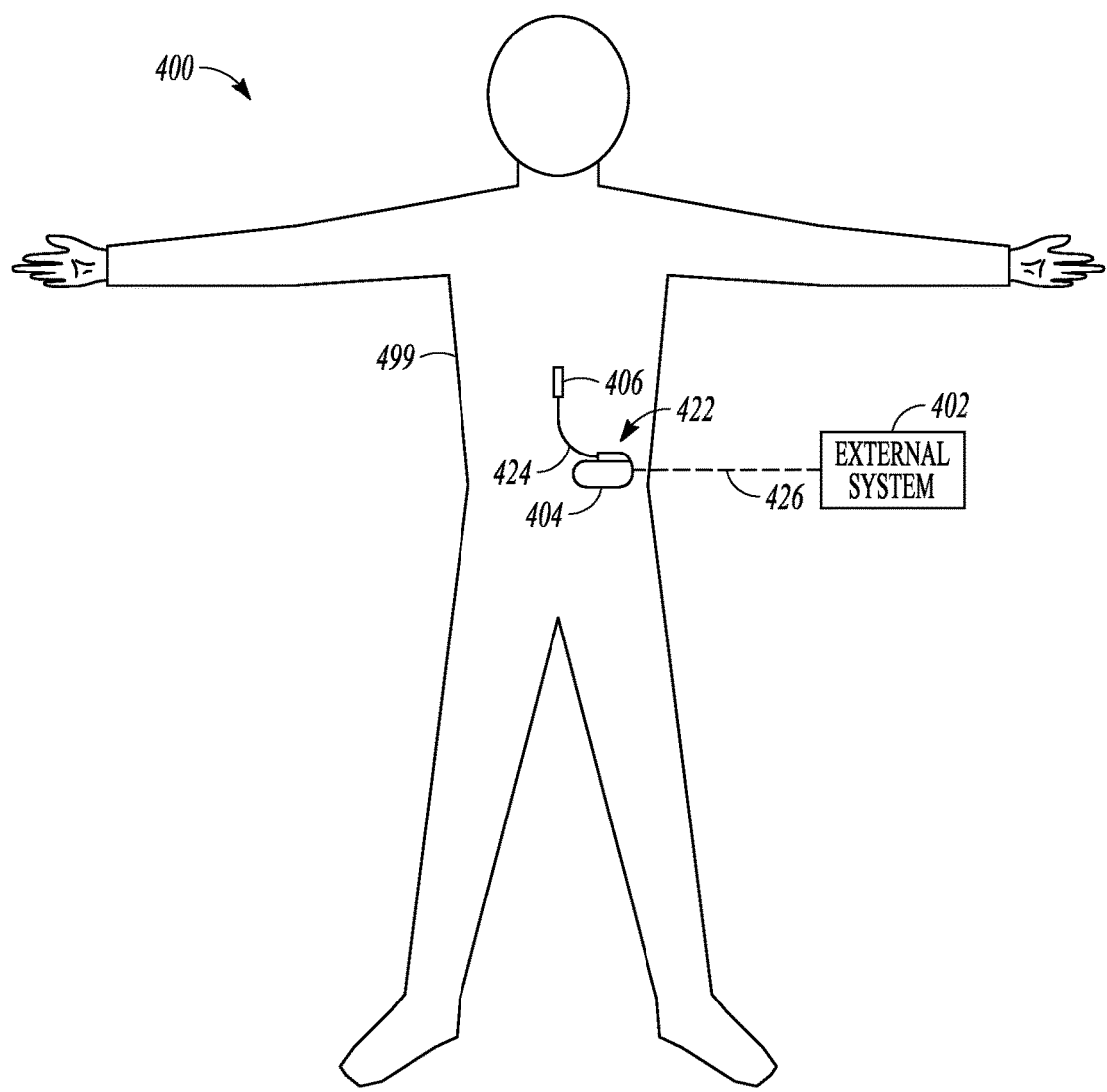
FIG. 4 illustrates an example of an implantable neurostimulation system.

FIG. 4 illustrates, by way of example and not limitation, an implantable neurostimulation system 400 and portions of an environment in which system 400 may be used. The system 400 may include an implantable system 422, an external system 402, and a telemetry link 426 providing for wireless communication between the implantable system 422 and the external system 402. In an example, the implantable system 422 is illustrated in FIG. 4 as being implanted in the patient's body 499.

The implantable system 422 may include an implantable stimulator (also referred to as an implantable pulse generator, or IPG) 404, a lead system 424, and electrodes 406, which represent an embodiment of the stimulation device 204, the lead system 208, and electrodes 206, respectively. The external system 402 may represent an example of the programming device 302. The external system 402 may include one or more external (non-implantable) devices each allowing the user and/or the patient to communicate with the implantable system 422. The external system 402 may include a programming device intended for the user to provide a user-perceivable input or receive a user-perceivable output and a remote control device intended for use by the patient. For example, the remote control device may allow the patient to turn the implantable stimulator 404 on and off and/or adjust a user-perceivable input or output. The sizes and shapes of the elements of implantable system 422 and their location in the body 499 are illustrated by way of example and not by way of restriction. In various examples, the present subject matter may be applied in programming any type of stimulation device that uses electrical waveforms as stimuli, regardless of stimulation targets in the patient's body and whether the stimulation device is implantable.

Figure 5:
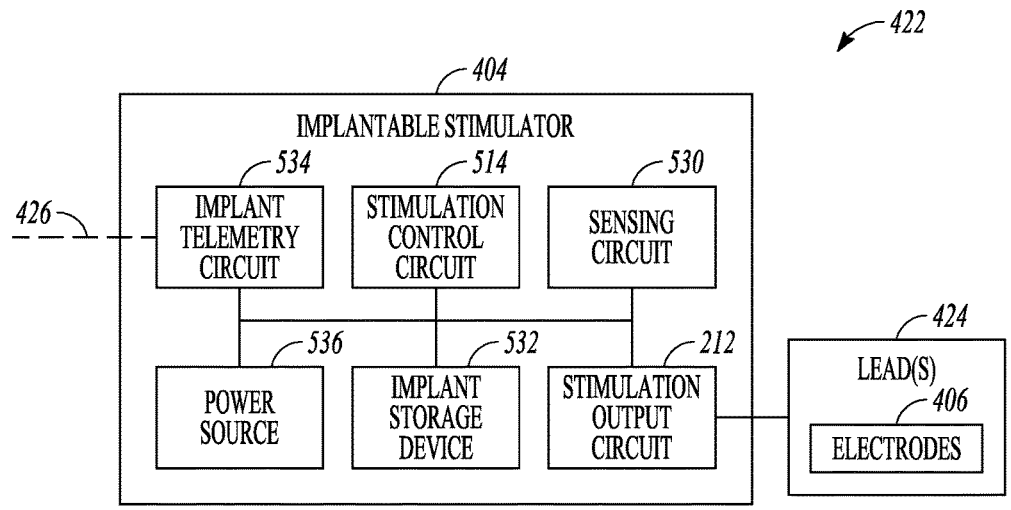
FIG. 5 illustrates an example of an implantable stimulator.

FIG. 5 illustrates, by way of example and not limitation, an embodiment of the implantable stimulator 404 and one or more leads 424 of an implantable neurostimulation system, such as the implantable system 422. The implantable stimulator 404 may include a sensing circuit 530, a stimulation output circuit 212, a stimulation control circuit 514, an implant storage device 532, an implant telemetry circuit 534, and a power source 536. The sensing circuit 530 may sense neural activity of the patient and provide the sensed activity to the external device 602 via the telemetry link 426. The stimulation output circuit 212 may be electrically connected to the electrodes 406 through the lead 424, and may deliver the neurostimulation through a set of electrodes selected from the electrodes 406. The stimulation control circuit 514 may represent an example of the stimulation control circuit 214 and may control the delivery of the neurostimulation based on the electrical waveform produced by the mapping controller 615. The implant telemetry circuit 534 may provide the implantable stimulator 404 with wireless communication with another device such as a device of the external system 402, including receiving values of the plurality of stimulation parameters from the external system 402. The implant storage device 532 may store values associated with electrical waveforms, such as those received from the mapping controller 615 or those sensed by the sensing circuit 530. The power source 536 may provide the implantable stimulator 404 with energy for its operation. The power source 536 may include a battery, such as a rechargeable battery and a battery charging circuit for charging the rechargeable battery. The implant telemetry circuit 534 may also function as a power receiver that receives power transmitted from the external system 402 through an inductive couple. In various examples, the sensing circuit 530, the stimulation output circuit 212, the stimulation control circuit 514, the implant telemetry circuit 534, the implant storage device 532, and the power source 536 are encapsulated in a hermetically sealed implantable housing. In various examples, the lead(s) 424 are implanted such that the electrodes 406 are placed on and/or around one or more targets to which the neurostimulation waveforms are to be delivered, while the implantable stimulator 404 is subcutaneously implanted and connected to the lead(s) 424 at the time of implantation. However, the present subject matter is not limited to use of implanted electrodes. A mapping controller as described above may be included in the implantable stimulator 404.

Figure 6:
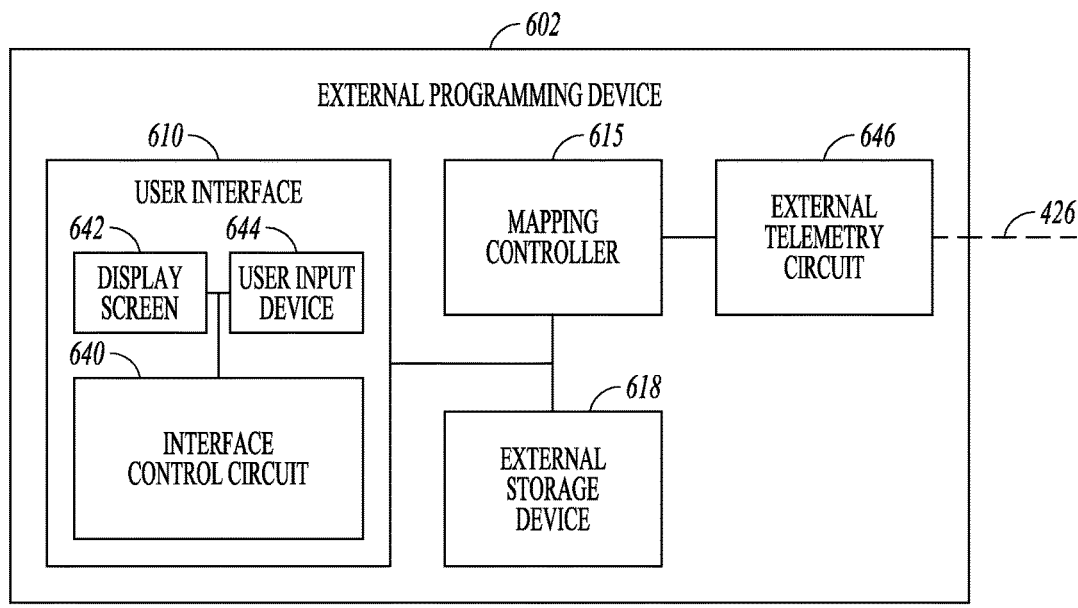
FIG. 6 illustrates an example of an external programming device.

FIG. 6 illustrates, by way of example and not limitation, an embodiment of an external programming device 602 of an implantable neurostimulation system, such as the external system 402. The external programming device 602 may represent an example of the programming device 302, and may include an external telemetry circuit 646, a mapping controller 615, an external storage device 618, and a user interface 610. The external telemetry circuit 646 may provide the external programming device 602 with wireless communication with another device such as the implantable stimulator 404 via the telemetry link 426, including transmitting an electrical waveform to the implantable stimulator 404. The external telemetry circuit 646 may also transmit power to the implantable stimulator 404 through the inductive couple.

The external storage device 618 may store an electrical waveform, such as that provided to the electrodes 406, to provide a therapy to the patient. Examples of such waveforms include pulses, bursts each including a group of the pulses, trains each including a group of the bursts, and sequences each including a group of the pulses, bursts, and trains. External storage device 618 may also store a plurality of stimulation fields. Each field of the plurality of stimulation fields may be defined by one or more electrodes of the plurality of electrodes through which an electrical waveform may be delivered over the one or more electrodes. The electrical waveform may include pulses, bursts of pulses, trains of bursts, and sequences of pulses, bursts, and trains. The electrical waveform may include a distribution of frequencies and amplitudes.

The mapping controller 615 may generate an electrical waveform, which may then be transmitted to the implantable stimulator 404. In various examples, mapping controller 615 checks values of the electrical waveform against safety rules to limit these values within constraints of the safety rules. The safety rules may be heuristic rules.

The user interface 610 may allow the user to compose a user-perceivable input that may define an electrical waveform for providing a therapy to a patient. The user interface 610 may include a GUI. The user interface 610 may include a display screen 642, a user input device 644, and an interface control circuit 640. The display screen 642 may include any type of interactive or non-interactive screens, and the user input device 644 may include any type of user input devices that supports the various functions discussed in this document, such as a touchscreen, keyboard, keypad, touchpad, trackball, joystick, mouse, and vibratory element. The interface control circuit 640 may control the operation of the user interface 610 including responding to various inputs received by user input device 644. The interface control circuit may include an audio circuit, a haptic circuit, and a color circuit for providing a user-perceivable output to the user. For example, the audio circuit may convert a received user-perceivable output signal from the mapping controller 615 and convert the received signal into an audio signal that may be listened to by the user.

The external programming device 602 may have operation modes including a composition mode and a real-time programming mode. In the composition mode (also known as the waveform pattern composition mode), the user interface 610 may be activated, while the mapping controller 615 may be deactivated. In an example, the mapping controller 615 does not dynamically update the electrical waveform in response to any change in user-perceivable input. In the real-time programming mode, both the user interface 610 and the mapping controller 615 may be activated. The mapping controller 615 may dynamically update the electrical waveform in response to changes in the user-perceivable input, and transmit the plurality of stimulation parameters with the updated values to the implantable stimulator 404.

Figure 7:
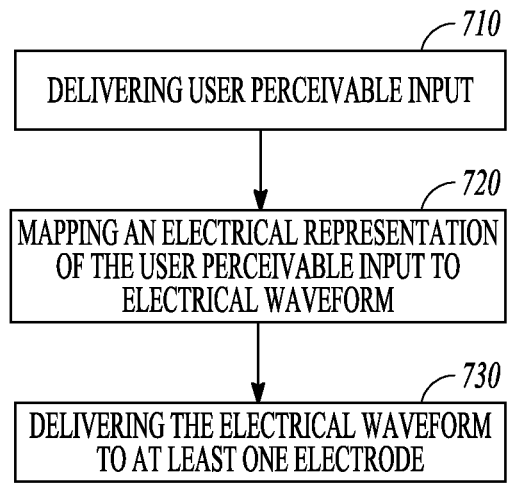
FIG. 7 illustrates an example of mapping a user-perceivable input to an electrical waveform.

FIG. 7 illustrates, by way of example and not limitation, a method for operating a neurostimulation system, such as neurostimulation system 100. The illustrated method may advantageously provide an improved method for composing complex electrical waveforms, such as the waveform 170 as shown in FIG. 1B. A complex electrical waveform, such as waveform 170, may include a collection of frequency and amplitude components and it may be difficult for the user to discern a recognizable pattern, let alone compose such a complex pattern. The user may provide a user-perceivable input to the user interface 110 (step 710). The user-perceivable input may be an audio signal, a haptic signal, or a color signal. The user interface may provide the user-perceivable input to the user, such as for the purposes of verification (e.g., if the user-perceivable input includes an audio signal, the user interface may play the audio signal to the user and the user may verify the audio signal). The mapping controller 115 may then map the user-perceivable input to an electrical waveform (step 720). The electrical waveform may then be delivered to the patient via at least one electrode to provide a therapy (step 730). The user-perceivable input may contain amplitude and frequency parameters of the delivered electrical waveform.

Figure 8:
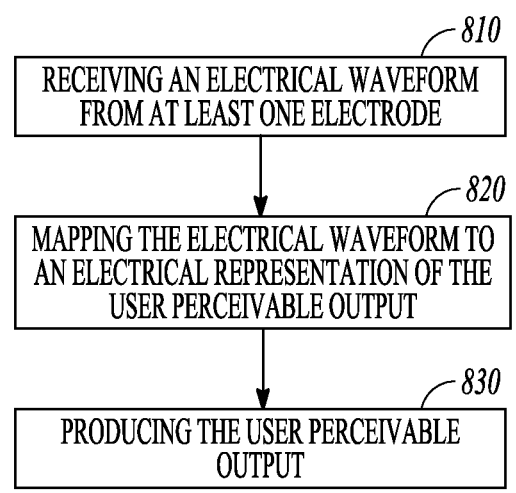
FIG. 8 illustrates an example of a method for mapping an electrical waveform to a user-perceivable output.

FIG. 8 illustrates, by way of example and not limitation, a method for operating a neurostimulation system, such as neurostimulation system 100. The electrodes 106 of neurostimulation system 100 may sense neural activity of the patient (step 810). The sensed neural activity may then be provided to the mapping controller 115 as an electrical waveform. The mapping controller 115 may then convert the electrical waveform into a user-perceivable output (step 820). Converting the electrical waveform may include scaling the electrical waveform. For example, when the user-perceivable output includes an audio representation of the electrical waveform, the frequency components of the electrical waveform may be reduced such that the audio representation of the electrical waveform may be within the human range of hearing. The mapping controller 115 may include a first mapping function for efferent neural waveforms and a second mapping function for afferent neural waveforms. The user-perceivable output may be generated based on the frequencies and amplitudes of the measured neural activity. The user-perceivable output may then be provided to the user interface 110. The user interface 110 may then provide the user-perceivable output to the user (step 830). The user interface may include haptic feedback circuitry configured to provide a haptic waveform corresponding to efferent neural waveforms to a first body location and a haptic waveform corresponding to afferent neural waveforms to a second body location (e.g., the user interface may provide vibrations to a user's left hand for efferent neural waveforms and may provide vibrations to a user's right hand for afferent neural waveforms).

The above detailed description is intended to be illustrative, and not restrictive. The scope of the disclosure should, therefore, be determined with references to the appended claims, along with the full scope of equivalents to which such claims are entitled.

The invention claimed is:

1. A method implemented by a system having processing circuitry, the method comprising:
   receiving a user-perceivable input comprising at least one of an audio signal or a haptic signal;
   determining an electrical waveform, using the processing circuitry, based on the user-perceivable input; and
   delivering the electrical waveform to at least one electrode, the at least one electrode configured to deliver neurostimulation to the patient.

2. The method of claim 1 wherein the user-perceivable input further includes a color signal.

3. The method of claim 2 wherein the user-perceivable input contains amplitude and frequency parameters of the delivered electrical waveform.

4. The method of claim 2 wherein the automatically determining includes a first mapping function for efferent neural waveforms and a second mapping function for afferent neural waveforms.

5. The method of claim 1 wherein the user-perceivable input includes the haptic signal, wherein the haptic signal has portions corresponding to efferent neural waveforms and to afferent neural waveforms.

6. A method implemented by a system having processing circuitry, the method comprising:
   receiving an electrical waveform from at least one electrode, the at least one electrode configured to sense neural activity in a patient;
   storing the received electrical waveform in a memory;
   determining, using the processing circuitry, a user-perceivable output based on the received electrical waveform; and
   producing the user-perceivable output to a first user, the produced user-perceivable output including at least one of an audio signal or a haptic signal, and being indicative of a healthy or diseased neural activity.

7. The method of claim 6 wherein the user-perceivable output includes the audio signal.

8. The method of claim 6 wherein the user-perceivable output includes the haptic signal.

9. The method of claim 6 wherein the user-perceivable output includes a color waveform.

10. The method of claim 6 further comprising:
    storing an electrical representation of the user-perceivable output in a memory;
    transmitting the electrical representation of the user-perceivable output and a mapping function to a user interface; and
    producing the user-perceivable output to a second user based on the transmitted electrical representation of the user-perceivable output and the mapping function.

11. The method of claim 10 wherein the mapping function includes a first mapping function for efferent neural waveforms and a second mapping function for afferent neural waveforms.

12. The method of claim 10 wherein the user-perceivable output includes a haptic waveform and the haptic waveform corresponding to efferent neural waveforms is provided to a first body location of the user and the haptic waveform corresponding to afferent neural waveforms is provided to a second body location of the user.

13. An apparatus comprising:
    at least one electrode configured to sense neural activity in a patient;
    a mapping controller configured to map the sensed neural activity to a user-perceivable output including at least one of an audio signal or a haptic signal; and
    a user interface operably connected to the mapping controller and configured to provide the user-perceivable output to a user.

14. The apparatus of claim 13 wherein the user-perceivable output includes the audio signal.

15. The apparatus of claim 13 wherein the user-perceivable output includes the haptic signal.

16. The apparatus of claim 13 wherein the user-perceivable output includes a color waveform.

17. The apparatus of claim 13 wherein the user-perceivable output is generated based on amplitudes and frequencies of the neural activity.

18. The apparatus of claim 13 wherein the mapping controller includes a first mapping function for efferent neural waveforms and a second mapping function for afferent neural waveforms.

19. The apparatus of claim 17 wherein the user interface includes haptic feedback circuitry configured to provide a haptic waveform corresponding to efferent neural waveforms to a first body location of the user and provide a haptic waveform corresponding to afferent neural waveforms to a second body location of the user.

\* \* \* \* \*